United States Patent
Fewster

(10) Patent No.: US 7,242,743 B2
(45) Date of Patent: Jul. 10, 2007

(54) X-RAY DIFFRACTION APPARATUS AND METHOD

(75) Inventor: Paul Frederick Fewster, Brighton (GB)

(73) Assignee: PANalytical B.V. (NL)

( * ) Notice: Subject to any disclaimer, the term of this patent is extended or adjusted under 35 U.S.C. 154(b) by 116 days.

(21) Appl. No.: 10/511,571

(22) PCT Filed: Apr. 10, 2003

(86) PCT No.: PCT/NL03/00272

§ 371 (c)(1),
(2), (4) Date: May 16, 2005

(87) PCT Pub. No.: WO03/087795

PCT Pub. Date: Oct. 23, 2003

(65) Prior Publication Data

US 2005/0226379 A1    Oct. 13, 2005

(30) Foreign Application Priority Data

Apr. 13, 2002   (GB)   .................. 0208572.8

(51) Int. Cl.
*G01N 23/20*   (2006.01)
(52) U.S. Cl. .......................... 378/71; 378/89
(58) Field of Classification Search ............. 378/70–90
See application file for complete search history.

(56) References Cited

U.S. PATENT DOCUMENTS 6,970,532 B2 *  11/2005  Hayashi et al. ............... 378/79

FOREIGN PATENT DOCUMENTS

JP   03-156350   7/1991
JP   2001-141674  5/2001

OTHER PUBLICATIONS

Noma et al., 'Surface-Sensitive X-ray Fluorescence and Diffraction Analysis with Grazing-Exit Geometry' X-Ray Spectrometry, vol. 28, 1999, pp. 433-439.*
"Grazing excidence diffraction versus grazing incidence diffraction for strain/stress evaluation in thin films" by Anouar Njeh et al.; *Powder Diffraction* 15 (4), Dec. 2000; pp. 211-216.
"Submicron x-ray diffraction and its applications to problems in materials and environmental science" by N. Tamura et al.; *Review of Scientific Instruments*; vol. 73, No. 3, Mar. 2002; pp. 1369-1372.
"Submicron X-ray diffraction" by A.A. MacDowell et al.; *Nuclear Instruments and Methods in Physics Research* A 467-468 (2001); pp. 936-943.
"Crystallographic Analysis of CVD Films by Using X-Ray Polychromatic Radiation" by B. Lavelle, et al.; 1998 *Materials Research Society Symp. Proc.* vol. 524; pp. 121-126.
"Image Plates as One-Dimensional Detectors in High-Resolution X-ray Diffraction" by A. Kinne et al.; *J. Appl. Cryst.* (1998); pp. 446-452.
"Real-time in situ x-ray diffractioin as a method to control epitaxial growth" by A.S. Bader et al.; *Applied Physics Letters*, vol. 82 No. 26; Jun. 30, 2003; pp. 4684-4686.

* cited by examiner

*Primary Examiner*—Edward J. Glick
*Assistant Examiner*—Jurie Yun
(74) *Attorney, Agent, or Firm*—Blakely Sokoloff Taylor & Zafman

(57) ABSTRACT

A high resolution X-ray diffraction apparatus includes a source 4 of X-rays and a slit 6 to direct a collimated beam of X-rays 11 onto a sample 16 on a sample stage 8. Detector 10 records the intensity of diffracted X-rays as a function of position along its length. The geometry allows high resolution without the use of a monochromator.

10 Claims, 5 Drawing Sheets ial application No. PCT/NL03/00272, filed Apr. 10, 2003.

The invention relates to an X-ray diffraction apparatus for high resolution diffractometrometry and a method of high resolution X-ray diffractometry.

The analysis of high quality thin layer materials, especially near perfect single crystal thin layer materials is valuable in determining layer thickness and composition of those materials. This approach may be used, for example, in the semiconductor industry.

High resolution X-ray diffraction is a well established technique for carrying out the analysis of such materials.

X-ray diffractometers have been used for many years for analysing perfect, nearly perfect and highly imperfect materials on a routine basis.

An early high resolution diffractometer is the double-crystal diffractometer which is illustrated in FIG. 1. An X-ray source 101 transmits X-rays to a collimating crystal 103 which directs them onto a sample 105 which can be rotated about an axis 107. The X-rays are diffracted by the sample 105 onto a detector 109. The sample is then rotated and the intensity of X-rays reaching the detector is measured as a function of the angle of this rotation. This structure is still widely used, and gives good results especially on perfect and near-perfect samples Unfortunately, double crystal diffractometers have a number of disadvantages. Firstly, the Bragg angle of the collimating crystal 103 has to match that of the sample 105. The matching of the collimating crystal and the sample crystal is very important and the resolution is fixed by the crystals. Accordingly, a different collimating crystal 103 is required for each new sample material.

Secondly, the X-rays in a double crystal diffractometer reach a large and ill-defined region of the sample. Since this ill-defined region is the region analysed, X-ray diffractometers do not give good results for non crystalline materials or materials with defects.

Thirdly, in a double crystal diffractometer a number of different wavelengths are diffracted into the detector simultaneously. This reduces the precision and resolution of the results if the sample 105 is bent.

Fourthly, there is a large background level of illumination that reaches the detector from imperfect samples which makes analysis of any results a problem.

Furthermore, the double crystal diffractometer is very sensitive to the alignment and significant changes can be observed with a tilt angle varying by only 0.2°. This makes the double crystal diffractometer difficult to set up.

A number of proposals to alleviate some of these problems have been made.

Bartels describes a diffractometer which removes the inconvenience of having to change the crystal in "Characterization of Thin Layers on Perfect Crystals with a Multipurpose High Resolution X-ray Diffractometer", Bartels, Journal Vacuum Science and Technology B Volume 1 page 338 (1983). Bartels replaced the collimating crystal of a double crystal diffactometer with two channel-cut monochromators which provide a good monochromator with a very narrow angular divergence. However, this change to the double-crystal diffractometer geometry does not solve many of the problems of the double-crystal diffractometer. In particular, the Bartels diffractometer cannot be used for interpreting complex diffraction patterns from all but the most perfect and flat samples.

Another prior art design is a triple-crystal diffractometer which overcomes the problem of a bent sample and produces a significantly improved diffraction profile. This is illustrated in FIG. 2. The triple crystal diffractometer differs from the double crystal diffractometer by having a further analysing crystal 104 interposed between the sample 105 and the detector 109. Each of the crystals is independently rotatable. The analyser acts as a detector with a very narrow angular acceptance.

Unfortunately, away from the position in which all three crystals have the same scattering angle the recorded intensity profile recorded at the detector broadens rapidly. Furthermore, alignment is very difficult and this configuration has accordingly only been used by a few research groups. Moreover, each new sample still requires a new collimating crystal.

The current state of the art commercial instrument is a multiple crystal diffractometer, in which the collimating crystal of the triple crystal diffractometer is replaced by a multiple crystal collimating arrangement, and the analyser has a channel cut crystal rotated about the axis of the sample.

Prior art high resolution systems are complex and difficult to set up and in particular take a significant time to record data since it is necessary to rock the sample, i.e. to adjust the angular position, to collect data. It would be beneficial to reduce the time taken to make measurements. Of course, such an increase in speed is particularly beneficial in production environments, though also worthwhile in any application.

Commercial diffractometers may be used in particular for quality control. In practice it is the double crystal approach that has traditionally been used, and the very difficult alignment of the triple-axis diffractometer is normally avoided. Although the multiple crystal diffractometer is an excellent research instrument, it has not replaced the simpler double crystal diffractometer for production line control. In view of the disadvantages of the double crystal configuration mentioned above there is a need for an alternative X-ray diffractometer suitable for routine use that addresses these disadvantages.

According to a first aspect of the invention there is provided an X-ray apparatus for high-resolution X-ray diffraction, comprising: a sample stage for holding a sample having a front face with the front face oriented substantially normally to a predetermined normal direction; a means for generating a collimated beam of X-rays at a predetermined target location on the sample stage at an angle of between 0° and 60° to the normal direction, the beam having an angular divergence at the sample stage in the range 0.01° to 0.20°; and an X-ray detector arranged laterally of the sample stage for detecting X-rays scattered by the sample to a predetermined range of angles to the normal direction, the angles in the predetermined range being in the range from 80° to 90°.

The inventive approach accordingly makes use of a means for generating a collimated beam of X-rays, a sample stage and a position sensitive detector. To take a measurement, a sample is mounted on the stage. The configuration of these components and the choice of reflection may be arranged to require no movement, or a very small movement of the detector for large detection angles, during data collection. Nevertheless, in spite of the simplicity of the arrangement high-resolution results may be obtained as explained below.

The prior art instruments such as a double-crystal or multiple-crystal diffractometer overcome wavelength dispersion of the X-ray source by various methods. Without compensation, the wavelength dispersion would broaden the measured peaks and destroy the high resolution required. For example, a multiple-crystal diffractometer works by isolating a single required wavelength. In contrast, the apparatus according to the invention overcomes dispersion by geometric arrangement.

To measure the X-rays scattered at a range in angles to create a profile of X-ray intensity versus angle the double-crystal and multiple-crystal diffractometers rotate the sample.

It might at first be thought that it would not be possible to achieve high resolution diffractometry by measuring a range of angles simultaneously. In order to carry out diffractometry in parallel, with a range of angles entering the detector at once, it is necessary that the beam used to probe the sample has a divergent range of angles. This could easily reduce the resolution.

However, by using the arrangement of the present invention, the scanning or angular spread is achieved through geometry. This has the significant benefit that a position sensitive X-ray detector may be used to measure the X-rays diffracted by the sample at different angles at the same time, i.e. in parallel, not sequentially. Accordingly, the use of the invention can greatly speed up the process of obtaining measurements from a sample. Hence, useable data can be collected from a typical semiconductor layer structure in one to ten seconds where a conventional high-resolution diffractometer would take one to ten minutes for comparable data.

The X-ray detector is located to measure X-rays scattered to a predetermined range of angles which predetermined range falls within the range of 80° to 90° inclusive from the normal direction. In other words, the X-ray detector measures X-rays diffracted by the sample that are emitted in a direction closely parallel to the surface.

This ensures that the angle subtended by a finite size illuminated area of the sample when viewed at the detector is as small as possible, thus increasing the resolution. As will be appreciated, the closer the diffracted beam gets to being parallel to the surface the smaller the projected area is as seen from the detector and accordingly the higher the resolution of the detector. Thus, preferably the detector is positioned to measure X-rays diffracted into the range of 85° to 90°, further preferably 88° to 90°.

A further feature of the invention is that the means for generating a collimated X-ray beam is arranged to generate a collimated beam that is not too far from the normal to the sample plane. As will be explained later, this geometry is useful in order that wavelength variation and beam spread do not give rise to excessive reduction in the high resolution. Preferably, the beam angle is less than 40° to the normal to the sample.

Preferably, the X-ray detector has a linear resolution in the normal direction of less than (i.e. better than) 0.002 times the distance from the X-ray detector to the predetermined target location. Further preferably, the linear resolution is better than 0.001 times the distance from the X-ray detector to the predetermined target location, or further preferably 0.0005 times the distance from the X-ray detector to the predetermined target location.

The means for generating a collimated beam of X-rays is preferably an X-ray source and a slit between the X-ray source and the sample stage. This allows a suitable beam to be provided without excessive difficulty or expense. Indeed, it is of particular benefit that the invention does not require an expensive monochromator to select only one X-ray wavelength to be incident on the sample.

Preferably, the X-ray source has a dimension of no more than 0.2 mm in the direction normal to the beam in the plane containing the normal, the incident beam and the scattered X-rays.

Preferably, the X-ray detector is an elongate X-ray detector extending in a direction parallel to the normal direction for detecting in parallel X-rays diffracted by the sample as a function of distance along the normal direction and hence over a predetermined range of angles to the normal direction. This allows measurements to be made in parallel over a range of angles. In an alternative arrangement a slit may be provided in front of an X-ray detector, and the slit moved to scan a range of angles.

Conveniently, the position sensitive X-ray detector is a solid state detector.

In another aspect, the invention relates to an X-ray apparatus for high-resolution X-ray diffraction of a sample having a substantially single crystal thin layer, comprising: a sample stage for holding a sample having a front face with the front face oriented substantially normally to a predetermined normal direction; an X-ray source for directing X-rays towards the sample stage; a slit arranged between the X-ray source and the sample stage, the X-ray source and slit being dimensioned and arranged to direct a collimated beam of X-rays at a predetermined target location on the sample stage at an angle of between 0° and 60° to the normal direction; an elongate X-ray detector arranged laterally of the sample stage for detecting X-rays diffracted by the sample as a function of distance along the length of the X-ray detector and hence over a predetermined range of angles greater than 80° to the normal direction.

According to a further aspect of the invention, there is provided an X-ray apparatus for high-resolution X-ray diffraction of a sample of predetermined type, comprising: a sample stage for holding a sample having a front face with the front face oriented substantially normally to a predetermined normal direction; a means for generating a collimated beam of X-rays at a predetermined target location on the sample stage at an angle of between 0° and 60° to the normal direction; and an X-ray detector arranged laterally of the sample stage for detecting X-rays diffracted by the sample at an angle of greater than 80° to the normal direction as a function of distance along the normal direction and hence over a predetermined range of angles to the normal direction, wherein the linear resolution of the X-ray detector in the normal direction and the means for generating a collimated beam are selected to achieve an angular resolution of at least 0.1° with a substantially single crystal sample of the predetermined material type.

The invention also relates to the use of an X-ray apparatus as set out above to measure a substantially single crystal thin layer sample mounted on the sample stage and oriented to diffract the collimated X-ray beam onto the position sensitive X-ray detector. The thin layer is preferably a semiconductor layer.

The invention also relates to a method of high-resolution X-ray diffraction, comprising providing an X-ray source and a slit for producing a beam of X-rays; providing a sample stage having a front face and an elongate X-ray detector located laterally of the sample stage extending longitudinally along a direction substantially normal to the front face; mounting a sample having a substantially single crystal thin layer material extending in a plane on the front face of the sample stage oriented to diffract a beam of X-rays incident from the X-ray source through the slit towards a direction substantially along the plane onto the X-ray detector; directing a beam of X-rays through the slit to the sample at an angle of 0° to 60° to the normal to the plane; and measuring with the X-ray detector the X-rays diffracted by the sample as a function of position along its length.

Preferably, the step of measuring the X-rays diffracted by the sample include recording the intensity of X-rays instant on the detector simultaneously at a number of different locations along the detector.

Embodiments of the invention will now be described, purely by way of example, with reference to the accompanying drawings in which.

Figure 1:
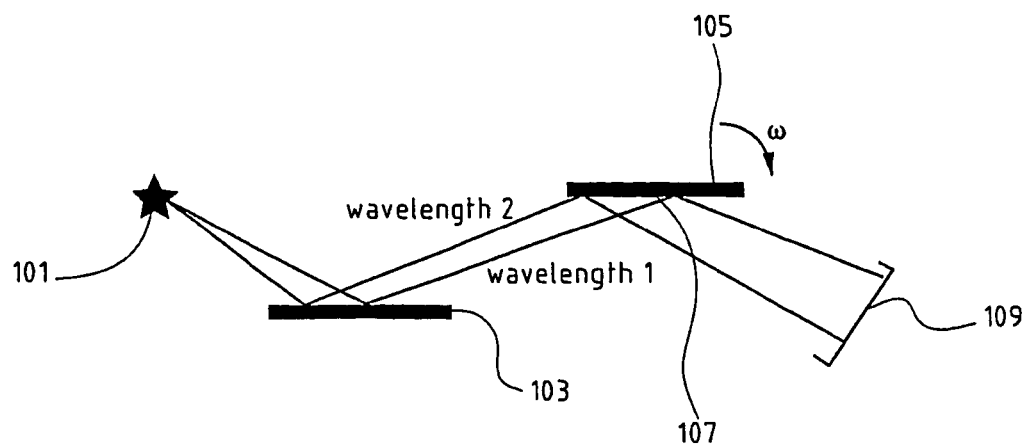
FIG. 1 shows a conventional double-crystal diffractometer.
Figure 2:
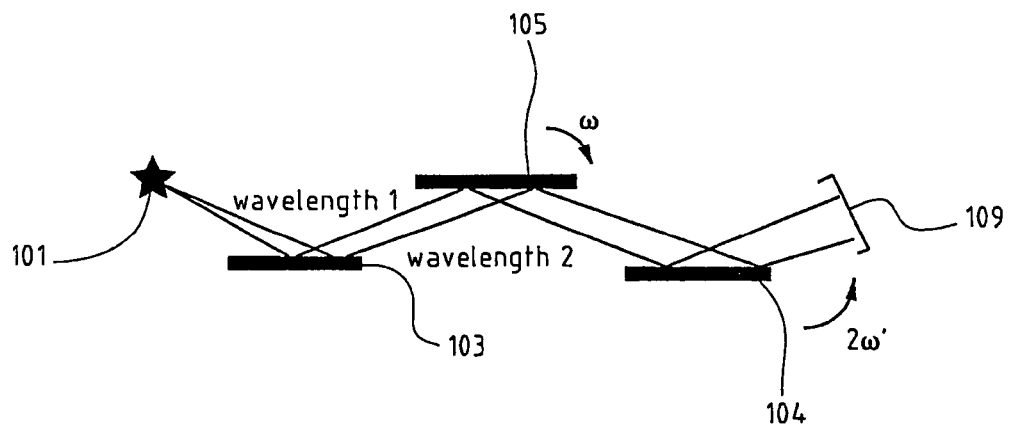
FIG. 2 shows a conventional triple-access diffractometer.
Figure 3:
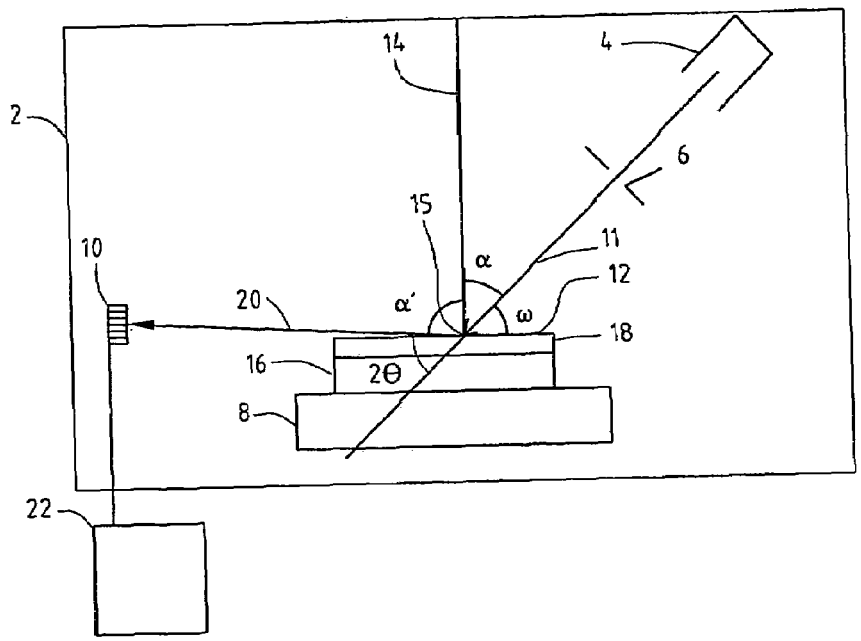
FIG. 3 shows a schematic drawing of an embodiment of the invention.

Referring to FIG. 3, the X-ray diffraction apparatus includes an X-ray enclosure 2, which holds the various components. An X-ray source 4 is arranged to emit X-rays through slit 6 towards sample stage 8. An elongate position sensitive detector 10 extends laterally of the sample stage along the normal to the front face 12 of the sample stage.

Any suitable X-ray source 4 may be used, including for example a cathode type X-ray apparatus or a synchrotron. In the specific embodiment, the X-ray source 4 produces CuKα X-rays.

The collimator 6 is arranged in front of the source 4 to direct a beam 11 of X-rays 11 at a target location 15 on the sample stage. The beam 11 is at angle of between 0° and 60° to the normal direction 14 to the sample stage 8.

In use, a sample 16 is mounted on the sample stage 8. The sample has a thin film 18 on its front face 12. Thus, the source 4 and slits 6 are arranged so that a beam of X-rays hits the thin film 18 on the front face 12 of the sample 16. The incident beam is incident at an angle α to the normal direction 14: α is given by α=90°−ω, where ω is the incident angle as conventionally defined.

The incident beam 11 is scattered or diffracted off the thin film 18 to the detector 10. The incident beam 11 is diffracted by a scattering angle 2θ to emerge at an angle closely parallel to the plane of the thin film 18 on the front face of the sample, at an angle α' to the normal. Because of the strain in the film with respect to the underlying substrate and the finite thickness of the thin film 18 the scattered beam 20 is emitted at a range of angles α' to the normal 14. The range of angles α' measured may be for example 85° to 90°. The position sensitive X-ray detector 10 can measure the X-ray intensity at a plurality of positions along its length simultaneously, and output this information to a data collection and recording device 22.

It will be noted that the scattered beam 20 is not at the angle that would result from a simple scattering by a plane parallel to the thin film 18 since the angle α is less than 60°, preferably less than 40°, whereas the angle α' is greater than 80° preferably greater than 85°. Thus, the X-rays measured are those scattered off the thin film 18 by crystal planes that are not parallel to the thin film 18 but inclined at angles to the thin film.

Figure 4:
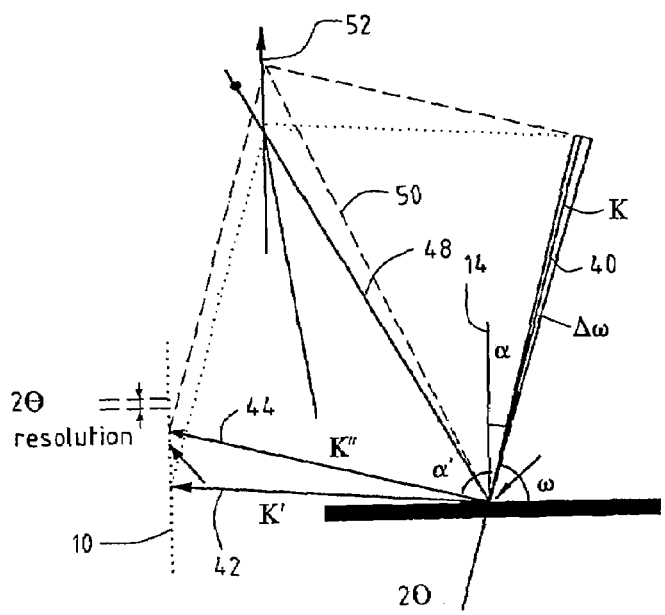
FIG. 4 illustrates the diffraction in reciprocal space.

The reason for this will now be explained with reference to FIGS. 4 and 5 which are diagrams of the arrangement of FIG. 3 scattering of thin film 18 shown in reciprocal space.

Vector K 40 represent the input beam. Vector K' 42 represents X-rays scattered at approximately 89° to the normal 14. Vector K" 44 represents X-rays scattered at a slightly different angle, here 85°, to the normal 14. As is known from conventional scattering theory, the magnitude of X-rays emitted in a direction K' is given by sample information in k-space at a location given by K'−k. Thus, the intensity of X-rays scattered into the direction of vector 42 is given by the intensity in k-space at radial vector 48 which is K'−k, whereas the intensity of radiation scattered into the direction of vector 44 is given by the intensity in k space of radial vector 50 given by K"−k. Thus, it will be seen from the drawing that a detector 10 that detects X-rays scattered to angles from the normal 14 of 85° to 89° samples information along a line 52 in k-space parallel to normal 14.

It should be noted that for samples that are substantially single crystalline the samples are accurately crystalline in the directions along the plane of the sample and accordingly give rise to a good 2-dimensional array of points in this plane. In contrast, the finite thickness of the thin film and possible inaccuracies and variations in its thickness give rise to sample information around each of the reciprocal lattice points in k-space that varies in a direction parallel to the normal 14. This variation in k-space gives information about the quality of the thin film. The sample information in k-space is thus represented by the points of the reciprocal crystal lattice spread substantially in a direction parallel to the normal 14 to the thin film but with little spread parallel to the thin film.

The X-ray detector detects the intensity of scattered X-ray radiation along its length, i.e. along a line parallel to the normal direction 14, and in so doing effectively scans nearly parallel to the line 52 in k-space and in so doing measures information about the quality of the thin film.

The geometric arrangement has further significant benefits which will now be described with reference to FIG. 5. Variation in wavelength of the incident beam causes uncertainty of the region in k-space scanned as represented diagrammatically by oval 54 in FIG. 5a. However, because the distribution of scattering around each reciprocal lattice point in k-space is effectively along line 52 normal to the sample surface, the spread in wavelength and corresponding spread in the sampled region of k-space 54 does not give rise to a significant smearing of the results since the spread 54 is not close to parallel to the line 52.

Figure 5A:
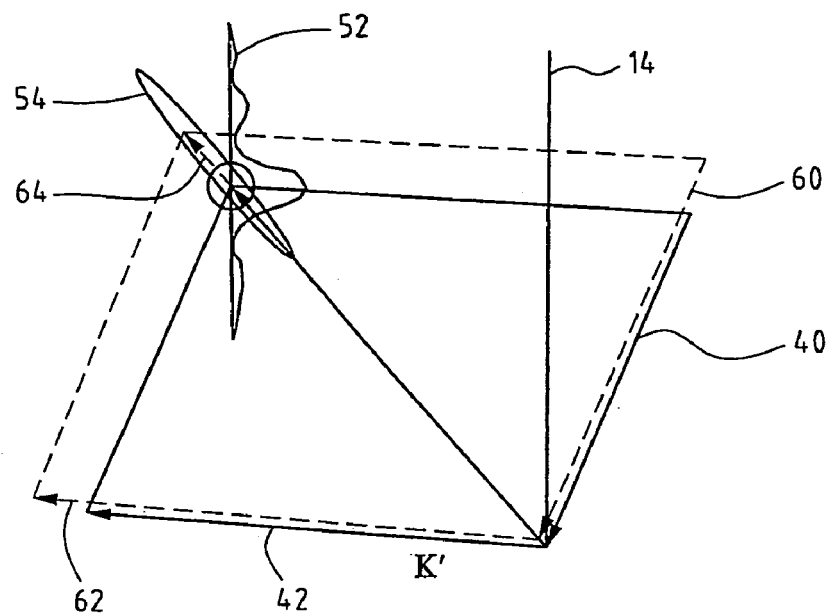
FIG. 5 illustrates the effect of various forms of incident beam deviation on the measured result.

To explain in more detail, FIG. 5a illustrates a nominal k vector 40 of input beam and K' vector 42 output. This scans the point in k space represented by vector 48 as discussed above. FIG. 5a also shows an input k vector 60 shown dotted which corresponds to a shorter wavelength. As a concrete example. vector 40 may correspond to one line of the CuKα doublet and vector 60 to the other line of the CuKα doublet. The shorter incident wavelength produces a scattered beam represented by vector 62 emitted in the same direction as K' vector 42. By vector addition, this scattering probes the point in k-space given by vector 64.

The oval 54 thus represents diagrammatically the variation in the probed region of k-space caused by variation in the wavelength of the incident beam. The oval in FIG. 5a is used for clarity in the Figure and is not intended to suggest an oval pattern of variation.

Vector 64 does not however probe a region of the k-space with additional sample information since the sample information is given by line 54 substantially along normal direction 14.

Thus the variation in the wavelength does not cause uncertainty in the position probed along line 52 parallel to normal 14, since the uncertainty 54 is along a different direction to the normal 14. Thus the wavelength uncertainty does not cause significant spread in the measured data.

Figure 5B:
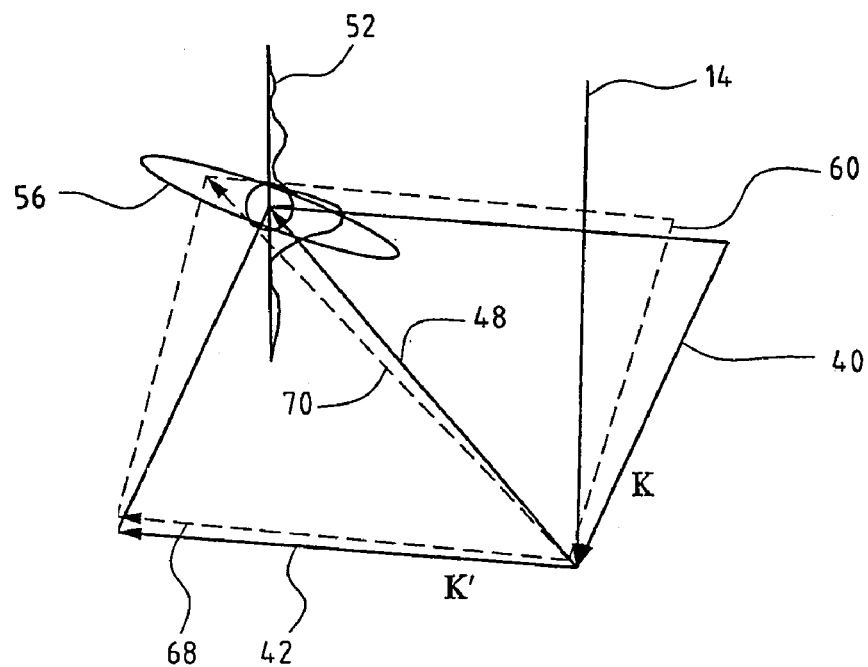

Similarly, FIG. 5b illustrates the effect of a divergent beam 66 at a different angle to nominal beam 40 yet scattering into the same direction as scattered beam 68. The uncertainty in the probed region of k-space is shown by oval 56. Again the uncertainty does not result in uncertainty along normal 52. Again it will be noted that the new radial vector 70 takes the probed point outside region 52 which contains sample information. Thus, again the moderate divergence does not cause excessive spread in the measured data.

The uncertainty 56 from beam divergence is inclined to the uncertainty 54 from wavelength variation by θ. It should be noted that although these two sources of divergence have been described separately, the complete instrument and sample effectively operate as a single instrument with a single spread in measured data.

The third important point about the geometry used is that because the scattered vectors 42, 44 are at a small angle to the plane of the sample, i.e. at an angle close to 90° to the normal to the plane of the sample, the angle subtended by a finite region on the sample surface is very small at the detector. If in contrast the detector were mounted directly above the sample there would not be a one to one correspondence between the location measured along the length of the the detector and the angle α' of emitted X-rays.

Thus, the geometric arrangement used, quite unexpectedly, allows high-resolution diffractometry to take place without the use of monochromators or complex arrangements such as the double-crystal diffractometer or the multiple-crystal diffractometer. In this context, "high resolution" refers to a diffractometer that is capable of observing thickness fringes from a layer up to about 0.1 micrometer thickness.

Further, the detector 10 can record data in parallel and thus measure the scattering information corresponding to a number of scattering angles simultaneously without the need to move the sample except for very large angular scans. Hence, useable data can be collected perhaps 50 times as quickly as previously.

The inventor has realised that it is possible to select suitable sizes of source 4 and slit 6 to obtain a beam that is sufficiently non-divergent for high resolution by using the geometry proposed. Calculations have been carried out to ascertain the range of suitable values of these sizes for a preferred embodiment. The preferred embodiment is suitable for probing Si and GaAs layers using a Cu Kα source.

The relevant parameter is the divergence at the sample 16 of the incident beam of X-rays 11 generated by the source 4 and slit 6. There is to some extent a trade-off. As the divergence is decreased below 0.06°, there is little improvement in resolution but some loss of intensity and some restriction in the range of information probed. As the divergence increases above 0.06° there is a significant increase in the wavelength band pass. For example, where the source of X-rays emits a Cu Kα doublet the Cu Kα2 component starts to appear and is very clear for a divergence of about 0.25°. An angle of divergence of 0.06° has been calculated to be about optimum. Thus, in this preferred embodiment, the angular divergence of x-rays at the sample is about 0.01° to 0.20°, preferably 0.02° to 0.10°, further preferably 0.03° to 0.06°.

The x-ray source preferably has a dimension perpendicular to the beam direction in the scattering plane (i.e. the plane of FIG. 6) of no more than 200 micrometers, preferably no more than 40 micrometers. In the geometric orientation proposed, the dimension out of the scattering plane can be large, even as high as 1 cm. In prior art approaches, so-called Soller slits are required, a series of parallel slits only passing beams parallel to within 0.2° of the scattering plane. It is a significant benefit of the invention that these are not required.

The arrangement of the invention is not sensitive to variation in the position of the sample. A rotation of the sample about the normal 14 does not degrade the signal, but only degrades the intensity by a factor of about 10 for a 5° rotation of the sample above or below optimal. Thus, it is not necessary to be excessively precise in orienting the sample—this increases the throughput of samples through the diffractometer.

Tilting the sample also has little effect. When the sample is tilted about an axis parallel to the surface and in the scattering plane then changing the tilt angle by 1° has little effect.

The incident angle α does require some adjustment to isolate the required $CuK\alpha_1$ wavelength. The incident angle α should accordingly be preferably set to an accuracy 0.01°, though 0.03° gives a workable high resolution profile.

A variation in the sample position along the normal axis is also not critical. A motion of plus or minus 0.5 mm has little effect on profile quality.

It will be appreciated that the sample needs to be oriented to diffract from a scattering plane that is not parallel to the front plane of the sample. In particular, the optimal plane has an incident beam as close as possible to the normal to the surface and an exit beam as close as possible to being parallel to the surface. The reason for this is that the uncertainty 54 is largely along the radial direction and it is necessary that this uncertainty does not lie parallel to the sample information which lies in a region of k-space 52 parallel to the normal direction 14. However, where α=α' the radial vector 48 is along axis 14 and thus the high resolution disappears. Instead, the smearing and uncertainty caused by X-rays of different wavelengths not all perfectly collimated probes a region of diffraction space that has significant scattering intensity at a number of positions, and accordingly causes smearing of the measured signal.

Thus, whereas conventionally a 004 scattering plane may be used, the scattering of the invention should use a different scattering plane such as the 113 reflection used in the example above. The 113 is a reflection that satisfies the condition that the incident beam can be near-normal and the exit beam near parallel to the surface for the commercially important materials Si and GaAs using CuKα wavelength X-rays.

In a specific implementation, the diffractometer has the following sizes. The distance of the slit to the sample $L_1$ is 320 mm, and the divergence of incident angle Δω 0.06°. This divergence is achieved by the source and slit in parallel. The distance of the detector from the sample $L_2$ is 240 mm. Using a 113 reflection, the angles shown in the figure are given by 2θ is 53.73° for GaAs and 56.12° for Si. ω is 52.1° for GaAs and 53.3° for Si. The detector slit width is 70 micrometers.

The inventor has calculated the resulting angular resolution $2\theta_{resolution}$ of the instrument to be given by:

$$2\theta_{resolution} \sim \{L_1[\tan(\Delta\omega)/\sin(\omega)]\sin(2\theta-\omega)/2+D/2\}/L_2$$

Putting in the values of the specific implementation, this gives an angular resolution of about 0.01° for both GaAs and Si samples. This is more than adequate for data collection. The angular resolution of 0.01° gives an increment corresponding to a film thickness of 1 micrometer. Therefore, the instrument is able to determine thicknesses up to about 0.3 micrometers, i.e. high resolution.

Figure 6:
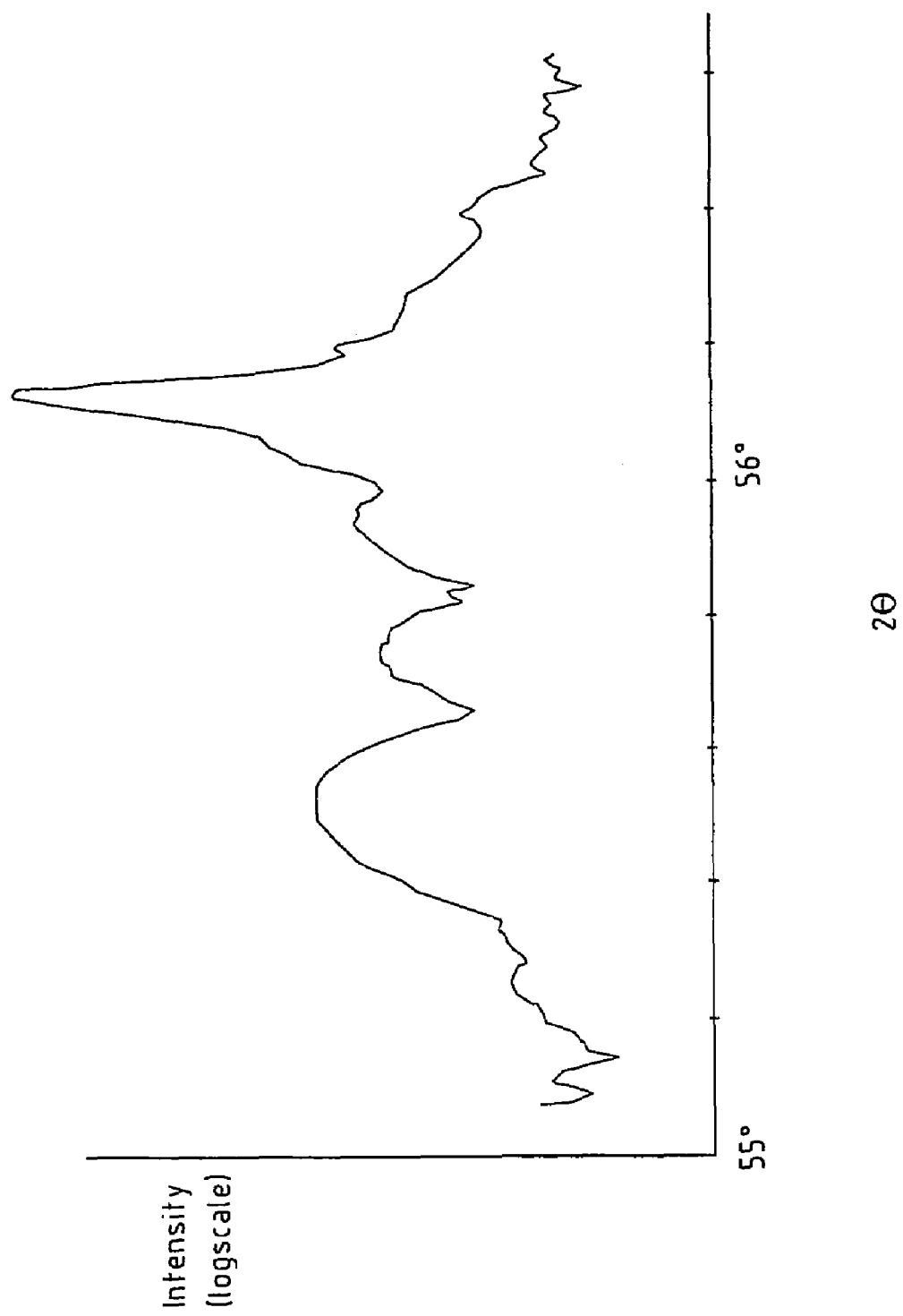
FIG. 6 shows results from a diffractometer according to the invention.
Figure 7:
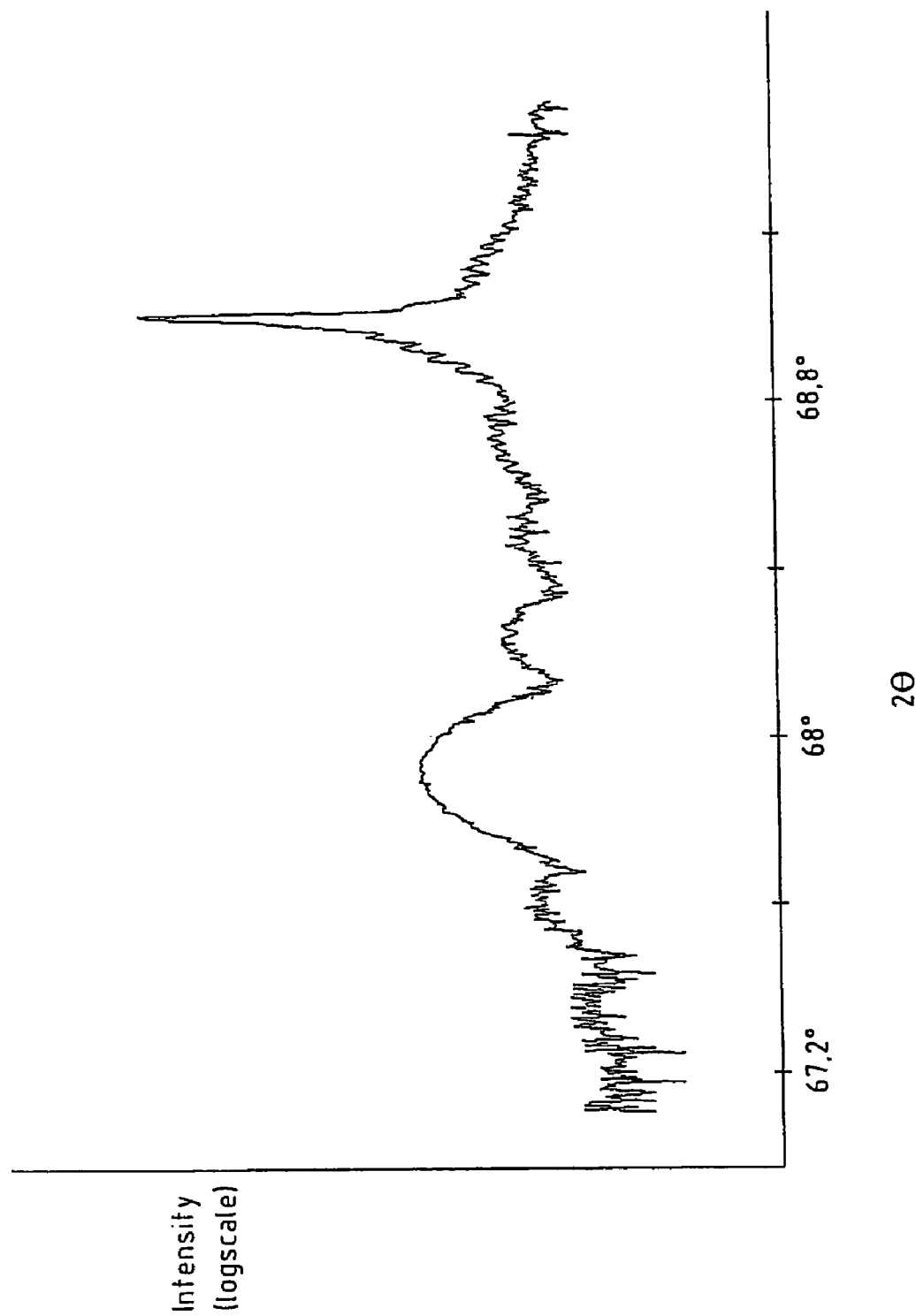
FIG. 7 shows results from a prior art high resolution diffractometer for comparison.

FIGS. 6 and 7 are measured results that illustrate the benefits of the invention. FIG. 7 shows the scattering intensity of a 113 reflection measured using a twenty second static scan on apparatus according to the invention.

FIG. 8 shows the scattered intensity of a 004 reflection for the same sample measured using a ten minute scan on a multiple crystal X-ray diffractometer. It will be seen that results of similar quality are obtained but at a very much greater speed using the apparatus according to the invention.

Note that FIG. 6 shows that the apparatus according to the invention is capable of a resolution $2\theta_{resolution}$ of significantly better than 0.1°.

Not merely is the apparatus according to the invention much faster, it is also much simpler, easier to set up and accordingly cheaper.

It will be appreciated that the arrangement of the present invention cannot be achieved in a conventional high-resolution diffractometer or double-crystal diffractometer apparatus. This is because in such prior art diffractometers data from any given incident angle arrives at the detector simultaneously with data from other incident angles and accordingly it is necessary to use an analyser such as used in the multiple-crystal diffractometer to resolve the situation.

From reading the present disclosure, other variations and modifications will be apparent to persons skilled in the art. Such variations and modifications may involve equivalent and other features which are already known in the design, manufacture and use of diffractometers and which may be used in addition to or instead of features described herein. Although claims have been formulated in this application to particular combinations of features, it should be understood that the scope of disclosure also includes any novel feature or any novel combination of features disclosed herein either explicitly or implicitly or any generalisation thereof, whether or not it mitigates any or all of the same technical problems as does the present invention. The applicants hereby give notice that new claims may be formulated to any such features and/or combinations of such features during prosecution of the present application or of any applications derived therefrom.

In particular, although in the embodiment described the detector is capable of detecting x-rays incident at a plurality of different incident locations in parallel, it may also be possible (though slower) to provide an arrangment that carries out the detection at a number of different incident locations in series, for example by providing a movable narrow slit in front of an X-ray detector.

The invention claimed is:

1. An X-ray apparatus for high-resolution X-ray diffraction of thin layers of single crystal, comprising: a sample stage (8) holding a sample (16) having a substantially single crystal thin layer (18) at a front face (12) with the front face (12) oriented substantially normally to a predetermined normal direction (14); a means (4,6) for generating a collimated beam of X-rays (11) at a predetermined target location (15) on the sample stage at an angle of between 0° and 60° to the normal direction, the beam having an angular divergence at the sample stage in the range 0.01° to 0.20°; and an X-ray detector (10) arranged laterally of the sample stage for detecting X-rays scattered by the sample (16) to a predetermined range of angles to the normal direction (14), the angles in the predetermined range being in the range from 80° to 90°, wherein the means for generating a collimated beam of X-rays comprises an X-ray source (4) and a slit (6) between the X-ray source and the sample stage, wherein the means for generating a collimated beam does not include a monochromator.

2. An X-ray apparatus according to claim 1 wherein the X-ray detector (10) has a linear resolution in the normal direction (14) of less than 0.002 times the distance from the X-ray detector to the predetermined target location.

3. X-ray apparatus according to claim 1 wherein the X-ray source (3) has a dimension of no more than 0.2 mm in the direction normal to the beam in the plane containing the normal, the incident beam and the scattered X-rays.

4. An X-ray apparatus according to claim 1 wherein the X-ray detector (10) is an elongate X-ray detector extending in a direction parallel to the normal direction (14) for detecting in parallel X-rays diffracted by the sample as a function of distance along the normal direction and hence over a predetermined range of angles to the normal direction.

5. An X-ray apparatus according to claim 1 wherein the X-ray detector (10) is a solid state detector.

6. An X-ray apparatus according to claim 1 wherein the substantially single crystal thin layer (18) is a semiconductor layer.

7. A method of high-resolution X-ray diffraction; comprising: providing a sample stage and an X-ray detector located laterally of the sample stage; mounting a sample having a substantially single crystal thin layer material extending in a plane on the sample stage; directing an incident collimated beam of x-rays created without a monochromator onto the sample at an angle of 0° to 60° to the normal to the plane; and measuring with the X-ray detector the X-rays diffracted by the sample to a range of angles in the range 80° to 90° to the normal to the plane; the X-ray detector thereby determining a thickness of the sample and outputting the results to a reading device.

8. A method according to claim 7 wherein the incident beam has an angular divergence in the range 0.01° to 0.20°.

9. A method according to claim 7 or 8 wherein the incident beam of X-rays is in a direction from 0° to 40° to the normal to the plane.

10. A method according to claim 7 or 8 wherein the step of measuring the X-rays diffracted by the sample (16) includes recording the intensity of X-rays incident on the detector (10) simultaneously at a number of locations along the length of the detector.

* * * * *

UNITED STATES PATENT AND TRADEMARK OFFICE
CERTIFICATE OF CORRECTION

| | |
|---|---|
| PATENT NO. | : 7,242,743 B2 |
| APPLICATION NO. | : 10/511571 |
| DATED | : July 10, 2007 |
| INVENTOR(S) | : Paul Fredrick Fewster |

It is certified that error appears in the above-identified patent and that said Letters Patent is hereby corrected as shown below:

In Claim #7, column 10 line 34, please delete "diffraction;" and insert -- diffraction --.

Signed and Sealed this

Twenty-ninth Day of April, 2008

JON W. DUDAS
*Director of the United States Patent and Trademark Office*